(12) United States Patent
Fedyk et al.

(10) Patent No.: US 7,066,870 B2
(45) Date of Patent: Jun. 27, 2006

(54) METHOD OF PRODUCING A CORRUGATED TAMPON APPLICATOR

(75) Inventors: Glen Charles Fedyk, Fairfield Township, OH (US); Nancy Karapasha, Cincinnati, OH (US); John David Norcom, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 232 days.

(21) Appl. No.: 10/179,087

(22) Filed: Jun. 25, 2002

(65) Prior Publication Data

US 2003/0236161 A1 Dec. 25, 2003

(51) Int. Cl.
*B31B 1/28* (2006.01)

(52) U.S. Cl. ............... 493/156; 493/152; 493/154; 493/178

(58) Field of Classification Search ............ 493/156, 493/152, 154, 167, 155, 172, 173, 174, 178
See application file for complete search history.

(56) References Cited

U.S. PATENT DOCUMENTS

| 3,683,759 | A | | 8/1972 | Voss |
| 5,330,421 | A | | 7/1994 | Tarr |
| 5,389,068 | A | * | 2/1995 | Keck ................... 604/15 |
| 5,571,540 | A | | 11/1996 | Weyenberg |
| 5,792,096 | A | * | 8/1998 | Rentmeester et al. ......... 604/14 |
| 5,909,884 | A | | 6/1999 | Schwankhart |
| 6,171,682 | B1 | | 1/2001 | Raidel |
| 6,264,626 | B1 | | 7/2001 | Linares |
| 6,358,223 | B1 | * | 3/2002 | Mackay et al. ............. 604/15 |
| 6,368,442 | B1 | * | 4/2002 | Linares et al. ............. 156/198 |
| 6,458,064 | B1 | * | 10/2002 | Balzar et al. ............. 493/330 |
| 6,582,389 | B1 | * | 6/2003 | Buzot ................... 604/15 |
| 6,685,787 | B1 | * | 2/2004 | Linares et al. ............. 156/198 |

* cited by examiner

*Primary Examiner*—John Sipos
*Assistant Examiner*—Christopher R. Harmon
(74) *Attorney, Agent, or Firm*—Ingrid N. Hickman; Kevin C. Johnson; Steven W. Miller

(57) ABSTRACT

A method of manufacturing a tampon applicator having a corrugated region, the method including the steps of:
a) providing a tampon applicator having a first end, a second end, a length and a diameter; and
b) forming a plurality of corrugations in the tampon applicator, the corrugations defining the corrugated region, each of the corrugations having a ridge and a trough.

4 Claims, 8 Drawing Sheets

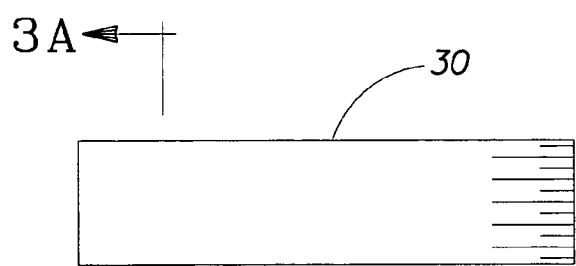 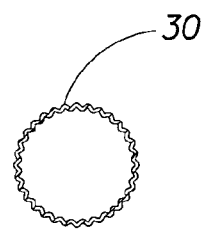
Fig. 3     Fig. 3A
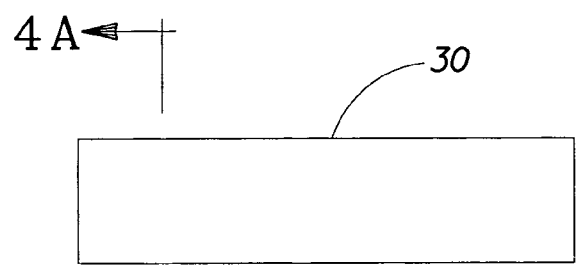 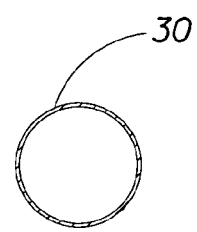
Fig. 4     Fig. 4A

METHOD OF PRODUCING A CORRUGATED TAMPON APPLICATOR

FIELD OF THE INVENTION

This invention relates to a method for corrugating and forming a tip and/or corrugating a grip on a hollow tube. More specifically, this invention relates to corrugating and forming an insertion tip in an end of a paper tampon applicator.

BACKGROUND OF THE INVENTION

Tampons and other types of absorptive media are routinely inserted into body cavities, such as a woman's vagina, to absorb menstrual fluid, blood and other kinds of body fluid. One convenient way to position such absorbent tampons into a body cavity is through the use of an applicator. Comfortable and clean insertion of the absorbent tampon is key to repeated sale of such applicators. In addition, the applicator should be capable of inserting the absorbent tampon into the body cavity using an acceptable amount of expulsion force.

Tampon applicators are available in a variety of shapes and sizes with the two-piece telescopically assembled design being the most prevalent. In the two-piece applicator, the tampon is housed in a hollow outer tube and is expelled into a woman's vagina by an inner member that is telescopically mounted in the outer tube and acts as a plunger. Some tampon applicators utilize a hollow tube having an open insertion end through which the tampon is always exposed while other applicators utilize a completely closed or partially closed design. A thin film membrane can cover the insertion end of an applicator to completely enclose the forward end of a tampon while folds can be used to partially enclose the forward end of a tampon and protect it from contamination. Still other applicators, especially plastic applicators, have a plurality of flexible petals formed on the forward end of the outer tube which can flex radially outward to allow the tampon to be expelled. It will be appreciated that the diameter of the applicator, the material from which it is formed, the basic configuration of the applicator, the size and shape of the tampon positioned in the applicator, as well as the ease of opening the forward end of the applicator will all influence the force required to expel the tampon therefrom. The expulsion force should be kept reasonably low to permit proper functioning of the applicator.

While many have tried to design and manufacture tampon applicators having these improved qualities, there still remains a need for a tampon applicator that is more comfortable to use. Those applicators having an open forward end tend to expose the dry absorbent fibers of the tampon to the interior walls of a woman's vagina and this can cause irritation during insertion. Commercially available plastic and cardboard applicators, using a plurality of petal tips separated by slots, can sometimes pinch or cut the vaginal tissue of a woman during insertion and cause discomfort.

U.S. Pat. No. 5,782,793 issued to Nielsen et al. discloses a tampon applicator having a semi-spherically shaped pleated tip. The pleats of Nielsen are formed by doubling the material upon itself and then pressing the material into place. As can be seen in FIG. 8 of Nielsen, the pleats 50 have a thickness dimension "t" defined by three layers of material 34. The doubling of material upon itself to form the pleats leads to high expulsion forces which can cause the applicator to deform or cause the tampon to be inserted incorrectly.

Applicators for delivering materials into a body cavity typically comprise a tubular insertion member having an insertion end and a gripper end opposite thereof, and an elongate expulsion member slidably fitted within the tubular insertion member for expelling the contained materials. The gripper end will generally incorporate features to allow a user to more or less securely hold the applicator during use, which includes the following steps: inserting the applicator into a body cavity, expelling a substantially enclosed material contained by the applicator, and withdrawing the applicator from the body.

Over the years, attempts have been made to improve the gripping features. One approach is to significantly reduce the diameter of the applicator in the gripper end. While a reduced diameter grip may help in preventing fingers from slipping during insertion, there is little or no resistance offered in the opposite direction during the expulsion step. This is a step with which many users have difficulty.

Another approach to improve the grip of the applicator during use is to incorporate projections, such as in the form of a ring, at the base of the applicator member being inserted into the body. Similar to the disadvantage of applicators employing a reduced diameter in the gripping end, projections typically provide only a single direction of resistance. In most cases, the resistance provided is intended to aid during the expulsion step.

While many have tried to design and manufacture tampon applicators having these improved qualities, there still remains a need for a tampon applicator that has gripping features that provide limited resistance to finger slip during use.

Common corrugation techniques such as those used in the production of corrugated paperboard or cart onboard package containers involve performing a process operation on a paper or fiber sheet or web that is generally planar in form when introduced into the corrugating process. Additionally, the sheet or web often contain two opposed side edges; and in the case of a sheet it often also possesses two opposed end edges.

For purposes of this invention, a tube blank is the structure subjected to a corrugating process and since a tube blank often does not possess opposed side edges (i.e. the surface of the tube blank is connected about the perimeter in a closed generally hollow form), and/or a tube blank is generally not planar when presented to the corrugating process. Therefore, non-planar corrugating techniques are required.

Accordingly, there is a need for a new and improved method of forming and corrugating an insertion tip on the end of the tampon applicator and corrugating and forming a grip for facilitating comfortable insertion of an absorbent tampon into a woman's vagina while having a low expulsion force.

SUMMARY OF THE INVENTION

The present invention relates to a method of manufacturing a corrugated tip and a corrugated grip. A method of manufacturing a tampon applicator having a corrugated region, the method including the steps of: providing a tampon applicator having a first end, a second end, a length and a diameter and forming a plurality of corrugations in the tampon applicator, the corrugations define the corrugated region, each of the corrugations having a ridge and a trough.

The inventive method of manufacturing a corrugated tampon tip is characterized by the steps of: providing a mandrel having a tip region and a tubular region; providing a forming cup; providing a tube blank; placing the tube blank over the mandrel; and pressing the tube blank into the forming cup. In an alternative embodiment, the tip region of the mandrel may have at least one perimeter less than a tubular region perimeter.

The inventive method of manufacturing a corrugated tampon tip is characterized by the steps of: providing a guide bushing; providing a tube blank; providing an inner dye gear; providing an outer dye gear; placing the tube blank over the inner dye gear; and rotating the inner dye gear and the outer dye gear.

The inventive method of manufacturing a corrugated tube blank comprises the steps of: providing a guide bushing; providing a tube blank; providing an inner dye gear; providing an outer dye gear; placing the tube blank over the inner dye gear; and rotating the inner dye gear and the outer dye gear.

This invention relates to catamenial tampons, and more particularly, to a method of producing shaped tampons. All documents cited are, in relevant part, incorporated herein by reference; the citation of any document is not to be construed as an admission that it is prior art with respect to the present invention.

BRIEF DESCRIPTION OF THE DRAWINGS

While the specification concludes with claims particularly pointing out and distinctly claiming the subject matter that is regarded as forming the present invention, it is believed that the invention will be better understood from the following description taken in conjunction with the accompanying drawings, in which:

FIG. 3 is a side view of a tube blank.

FIG. 3A is a cross-section taken along lines 3A—3A of FIG. 3

FIG. 4 is a side view of an alternative embodiment of the tube blank.

FIG. 4A is a cross-section taken along line 4A—4A of FIG. 4.

DETAILED DESCRIPTION OF THE INVENTION

The present invention provides a new and improved method of corrugating and forming a tip and/or corrugating a grip on a hollow tube. More specifically, this invention relates to corrugating and forming an insertion tip in the end of a paper tampon applicator.

Section A. will provide terms which will assist the reader in best understanding the features of the invention and not to introduce limitations in the terms inconsistent with the context in which they are used in this specification. These definitions are not intended to be limiting. Section B. will discuss the tampon applicator that results from the method of making the corrugated tip and corrugated grip tampon applicator. Section C. will discuss the different stages of the method of manufacturing a corrugated tampon tip and a corrugated grip.

A. Terms

The term "tampon" refers to any type of absorbent structure which is inserted into the vaginal canal or other body cavities for the absorption of fluid therefrom. Typically, tampons are constructed from an absorbent material, which has been compressed and/or shaped in any or all of the width direction, the radial direction, and the axial direction, in order to provide a tampon which is of a size and stability to allow insertion within the vagina or other body cavity. A tampon has a "self-sustaining shape" when a tampon pledget has been compressed and/or shaped such that it assumes a general shape and size which is vaginally insertable absent external forces. It will be understood by one of skill in the art that this self-sustaining shape need not, and preferably does not persist during actual use of the tampon. That is, once the tampon is inserted and begins to acquire fluid, the tampon may begin to expand and may lose its self-sustaining form.

As used herein the terms "vaginal cavity", "within the vagina", and "vaginal canal" are intended to be synonymous and refer to the internal genitalia of the human female in the pudendal region of the body. The term "vaginal canal" is intended to refer to the space located between the introitus of the vagina (sometimes referred to as the sphincter of the vagina) and the cervix and is not intended to include the interlabial space, including the floor of vestibule. The externally visible genitalia generally are not included within the term "vaginal canal" as used herein.

Figure 2:
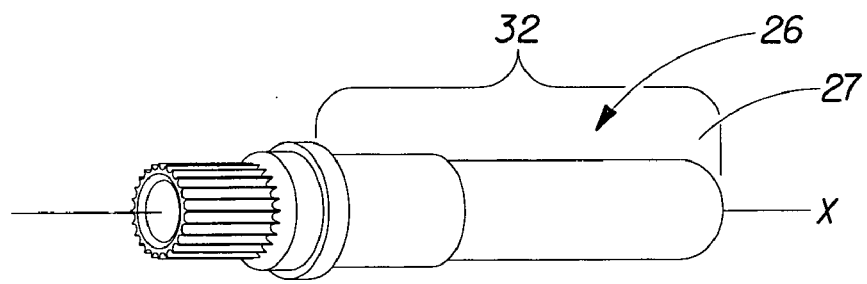
FIG. 2 is a perspective view of the mandrel.

The "X axis" of a mandrel is the axis which runs longitudinally through the center of the mandrel as shown in FIG. 2. A portion of the mandrel may be asymmetric about the X axis, such as during the manufacturing process. Further, the X axis may be linear or non-linear. The "perimeter" of a segment of the mandrel is a distance measured around the outer surface of the mandrel perpendicular to the X axis. A "perimeter line" is created by the intersection with the outer surface of the mandrel of a cross-section plane drawn perpendicular to the X axis. The perimeter is the length of this perimeter line. In cases where the X axis is non-linear, the cross-section plane is drawn perpendicular to a line tangent the X axis at the point of interest.

The term "tube blank" refers to a hollow tube before the manufacturing process.

The term "tapered" refers to a gradually narrowing portion of a mandrel. A tip region is "tapered" when the insertion end or a portion thereof has a plurality of gradually decreasing perimeters approaching the edge of the mandrel.

A "circumscribed perimeter" of a tube blank or tube is a distance measured around the outer surface of the tube blank or tube where the perimeter segments are measured from projection to projection about the perimeter in those places of the tube or tube blank where a smooth perimeter is not present. For example, the circumscribed perimeter of a tube that is corrugated about its perimeter would be measured by totaling distance of the segments between the tops of the ridges of the corrugations and not the measure of the distance down the slope into the valley and then up the slope between adjacent corrugation ridges.

B. Description of the Tampon Applicator

Figure 1:
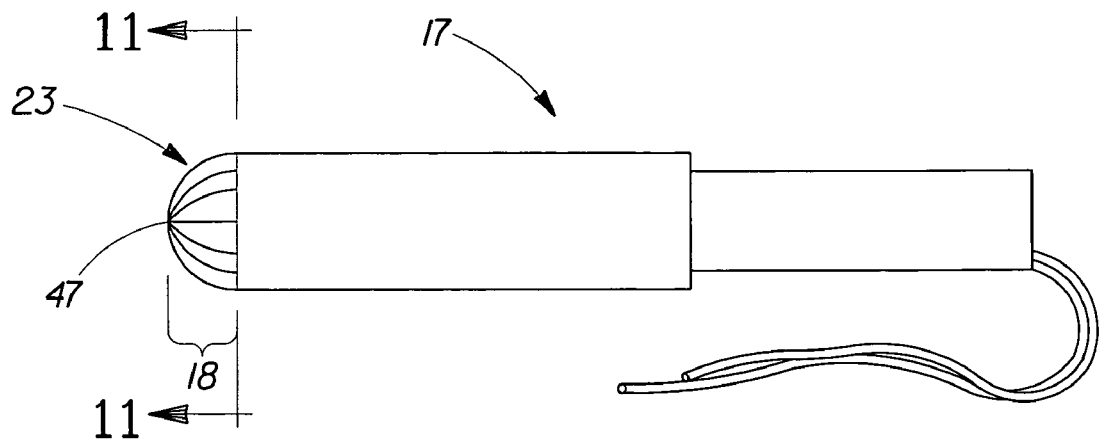
FIG. 1 is a side view of the tampon applicator.
Figure 8:
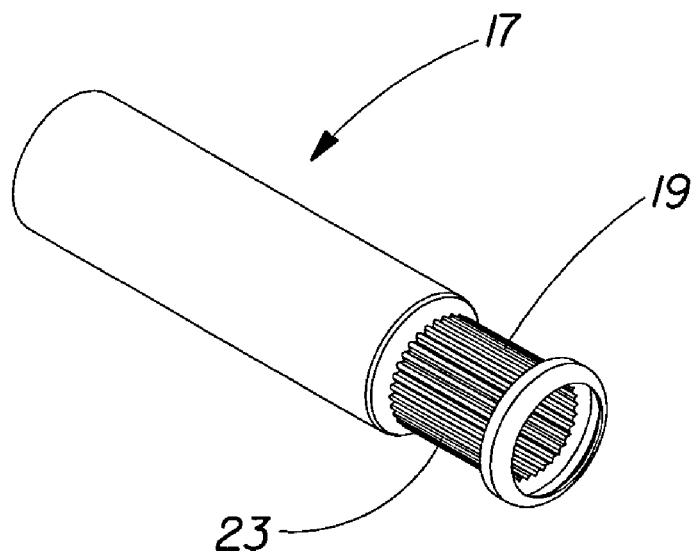
FIG. 8 is a perspective view of the tampon applicator with a corrugated grip region.
Figure 11:
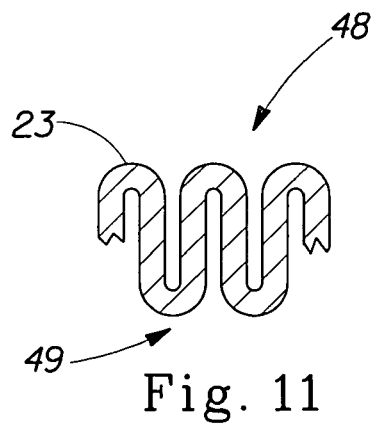
FIG. 11 is a schematic view of some corrugations taken along line 11—11 of FIG. 1 depicting the shape and thickness of the corrugations.

While the method of the present invention can be useful in producing any size or shape tampon applicator, the method of the present invention is particularly useful for producing tampon applicators having at least one corrugation, which can readily be seen, for example, in FIG. 1 and FIG. 8. Referring to FIG. 1, the elongate insertion member 17 can have the insertion tip 18 formed into a desired corrugated configuration with the central aperture 47 by using the method described below. Referring to FIG. 11, the corrugated tip 23 consists of a plurality of ridges and troughs formed about the circumference of the first end 25 of the tube blank 30. Also, referring to FIG. 8, the elongate insertion member 17 can have the grip 19 formed into a desired corrugated configuration by using the method described below.

Tampon applicators having this design are described in greater detail in co-pending case Ser. No. 10/179,808, filed Jun. 25, 2002, entitled "Tampon Applicator Having a Corrugated Insertion Tip", to Fedyk et al., and co-pending case Ser. No. 10/179,136, filed Jun. 25, 2002, entitled "Tampon Applicator Having a Corrugated Grip", to Fedyk et al.,.

C. Method

The method for corrugating and forming a tip and/or corrugating a grip on a hollow tube can be accomplished by employing any combination or sequence chosen from the group of the three steps described below. Each step can be repeated in a contiguous or skipped order or steps can be omitted with the only requirement that the corrugation step be executed at least once during the method of manufacture. The three steps are the (1) softening step; (2) corrugation step; and (3) final closure step. Again, the sequence and the number of times each step is performed can be any combination as long as the corrugation step is performed at least once. Further, sub-steps of each of the steps can be performed in any order or even processed where sub-steps of two different steps are interspersed in time sequence with each other or even done concurrently.

1. Softening Step

The softening step is used to change the modulus of the paper or fiber structure of the tube in the region of interest. This can be done singly or multiple times before or after one or several corrugation steps. The change of modulus in the region of interest results in the tube structure being more flexible, pliable or bendable than the original state prior to the softening step. Sometimes in addition to being more flexible, pliable or bendable the softened region will feel softer.

Figure 7:
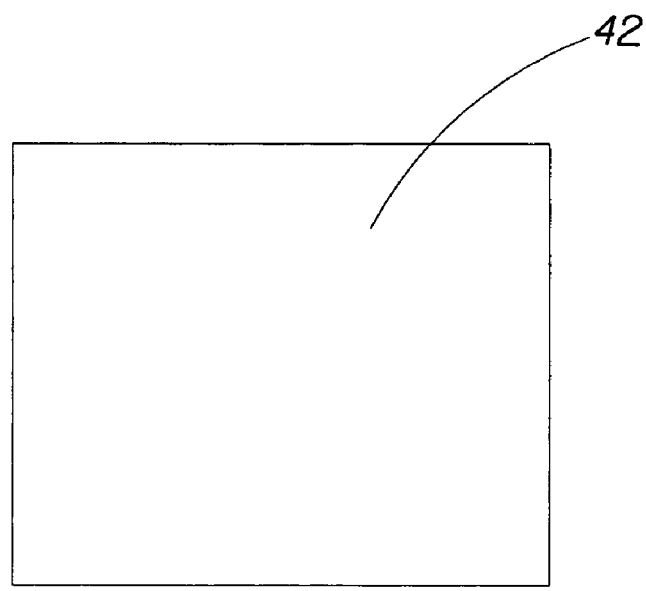
FIG. 7 is a perspective view of the flat dye.

Softening can be accomplished by any known means though preferably they are either mechanical or chemical. An example of a mechanical softening means is a flat dye 42. As shown in FIG. 7, the flat dye 42 can be any shape as desired as long as the flat dye has at least one substantially flat surface. A broad example of mechanical softening is single or multiple folding of sections of the region where two sections adjacent to the foldline change in relation to each other about the foldline during manufacture of the planar relationship of the two sections. Optionally, the two sections can be returned to the original planar relationship prior to the softening step or be left in a different planar relationship in relation to each other at the conclusion of the softening step. A region can be folded with multiple foldlines or multiple times. A foldline can be in any spatial orientation relative to another foldline, e.g. parallel, skewed, intersecting. Crumpling of material often results in multiple foldlines with some intersecting.

The foldline itself may or may not leave a witness mark or line after completion of the softening step. Some examples of witness marks or lines are creases, surface breakage, ridges, and offset planes. In the case of more severe folding which approaches 180 degree planar offset of the two sections about the foldline, witness marks are more likely to be formed. In the case of less severe folding such as gentle bending or flexing, the likelihood of the presence, noticed by the naked human eye or detected by human feel of the witness mark or line is decreased.

Optionally, the folding process can be assisted with a tool comprising a folding edge such as a straight edge about which the foldline is created where the planes of the two sections on either side of the foldline are offset from their original spatial relationship using the folding edge as a folding or bending axis. Repetition of a folding, bending or flexing operation can be useful such as repeated folding or bending back then forth, inverting and un-inverting, crumpling and expanding, compression (e.g. radial or planar), and re-expansion, etc.

Use of an implement during softening can also permit softening by curling a region of interest, by drawing the paper or fiber structure about a radiused edge such as common when curling certain types of decorative giftwrapping ribbon with the edge (or curling edge) of a knife or scissors blade. The curling edge radius; the angle of approach and the angle of exit between the paper or fiber structure region and the curling edge; and the frictional relationship between the curling edge and the paper or fiber structure can be varied to effect different degrees of softening.

Another example of a softening technique is scoring. One type of scoring is to cut into the paper or fiber structure. Minimal cut scoring breaks at least one surface of either face of the tube while more substantial cut scoring penetrates deeper into the paper fiber structure thickness, preferably not fully through the structure though in some cases that may be appropriate. Cut scoring can be accomplished by any known means including but not limited to the use of knives, rotary knives, lasers, blades, saws (which is one toll that can optionally remove some material such as removing some fibers), water jets, wires, etc. Another type of scoring is compressive scoring where the use of an implement (e.g. a straight or rotary edge) creates a continuous or discontinuous line (e.g. straight or curved) where the density within the compressive score line is higher than the original density and is generally higher than one or more immediately adjacent sections of the tube. Compressive scoring also decreases the caliper of the material in the score line versus its original caliper. A most preferred compressive score line exhibits a high density gradient between the score line and at least one of the immediately adjacent sections. A score line, either cut or compressive, can be in any spatial orientation relative to another score, e.g. parallel, skewed, intersecting.

Another softening technique involves embossing either in continuous or patterned fashion. One type of embossing form is compressive embossing where the embossed area exhibits a density increase and a caliper reduction versus its original properties. Another form of embossing is displacement embossing where the embossed area is altered such that the majority of the embossed area, excluding the transition zones adjacent the unembossed tube sections, is moved away from its original plane to another plane, often generally parallel to its original plane though this is not required. The area of embossment and type of pattern can vary as appropriate. Further embossments can be combined with other embossments, score lines or folds.

Another softening technique involves chemical softening such as the addition of any agent that at least partially inhibits, disrupts or displaces the formation of bonds between fibers, e.g. hydrogen bonds. Not to be bound by any theory, but at least two mechanisms can be used: 1) impregnate the paper with a liquid that itself forms hydrogen bonds with the fibers (thus reducing the number of hydrogen bonds between fibers); or 2) impregnate the paper with a low-polarity solvent, that causes weakening of the bonds between fibers due to its dielectric constant. Example of possible hydrogen bond disruption, inhibition or weakening agents include the addition of glycerol, polyethylene glycol, other glycols, chemicals exhibiting hydroxyl or amine functionalities, or chemicals with sulpher-containing groups.

2. Corrugation Steps

The corrugation step creates one or more corrugates in the region of interest of the tube blank 30. For the purposes of this invention, the corrugation step involves non-planar corrugating techniques.

Referring to FIGS. 3 and 4, the tube blank 30 is formed before the insertion tip 18 or the corrugated grip 19 is formed. At this stage, the hollow elongate cylindrical insertion member 17 has an essentially constant inside diameter and the wall has a constant thickness.

The reference to a corrugation step means that the corrugation step involves the use of non-planar corrugation techniques where at least one of the sub-steps is performed on the tube blank when the blank is in a non-planar and/or closed form. While all the sub-steps of the corrugation step may be performed on the tube blank when the blank is in a non-planar and/or closed form, some of the sub-steps (or even all except for one sub-step) can be executed on the tube blank or its components prior to the tube blank being fully made or shaped into either a closed or non-planar form. For example some of the sub-steps can be executed on the paper webs used in a composite tube blank where the tube is formed into a spirally wound, convolutedly wound or longitudinally seamed hollow tube which is formed from paper, paperboard, cardboard or a combination thereof. Another illustration to demonstrate the flexibility of the method is that one, some or all sub-steps of the corrugation step can be performed on a larger (e.g. longer) tube blank that is later cut into smaller tubes. Any or all of the sub-steps of the softening step can also be performed on the tube blank or its components prior to the tube blank being fully made or shaped into either a closed or non-planar form.

The corrugation steps (or steps) can produce any number of corrugates based on the need. Either an even or an odd number of corrugations 23 can be present and the corrugations 23 can be equally spaced apart or they can be non-uniformly arranged. Uniformly arranged corrugations 23 are preferred but randomly arranged corrugations 23 will work. For ease of manufacturing, it is preferred that the corrugations be equally spaced relative to one another. The corrugations 23 may be unequally spaced relative to one another. Referring to FIG. 11, the corrugations are formed by folding the material into a series of alternating ridges 48 and troughs 49 where the transition radius at the fold between two adjoining trough or ridge walls can be tight analogous to the bottom of the capital letter "V" in Arial typefont or more gentle or curved analogous to the bottom of the capital letter "U" in Arial type-font. Further, the corrugations can be tilted such that the cross-section appears like italicized capital letters "U" and "V" in Arial type-font.

The corrugations 23 for a given area of interest on the tube may be formed to have essentially identical lengths. Alternatively, the corrugations may be of differing lengths. For example, the lengths of the corrugations may be selected to alternate between a first length dimension and a second length dimension which are different from one another. The differing lengths may be random or arranged in a pattern. The number of differing length dimensions may be more two or more.

Further, the corrugation shape and orientation can vary. For example the corrugations may form lines that parallel or lie within a given radial plane. Alternatively, the corrugations may form curves or spirals that cross several radial planes. The corrugations may also include cuts to improve the fold or unfolding of the insertion tip. The cuts can comprise scores on either the interior or exterior surface, small perforations, or even longer cuts, which could create sidewall slits or even discrete petals. The cuts can be oriented and located in any direction or region of the insertion tip as desired.

As illustration of non-planar corrugating techniques, four example techniques are described below. They are a) rotary nip; b) axial swaging; c) radial compression; and, d) circumscribed perimeter reduction. These techniques and other non-planar corrugating techniques can be used in whole or part exclusively for a given tube blank or in combination of two or more techniques or elements thereof. One technique or combination of techniques may be found more useful depending on the feature to be formed on/in the tube blank, e.g. tube tip or tube grip.

a. Rotary Nip Technique

Figure 5:
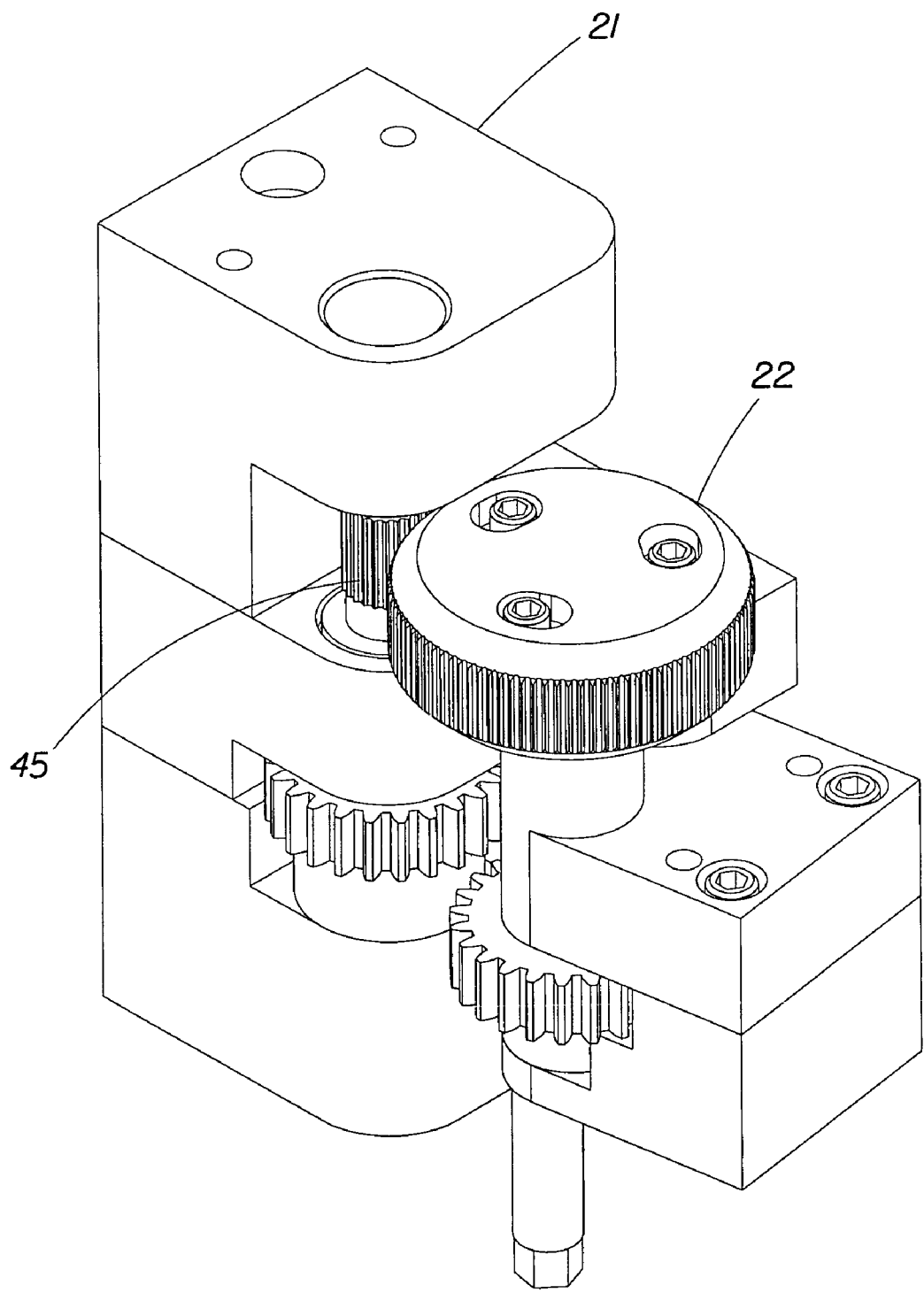
FIG. 5 is a perspective view of the guide bushing and outer dye gear.
Figure 12:
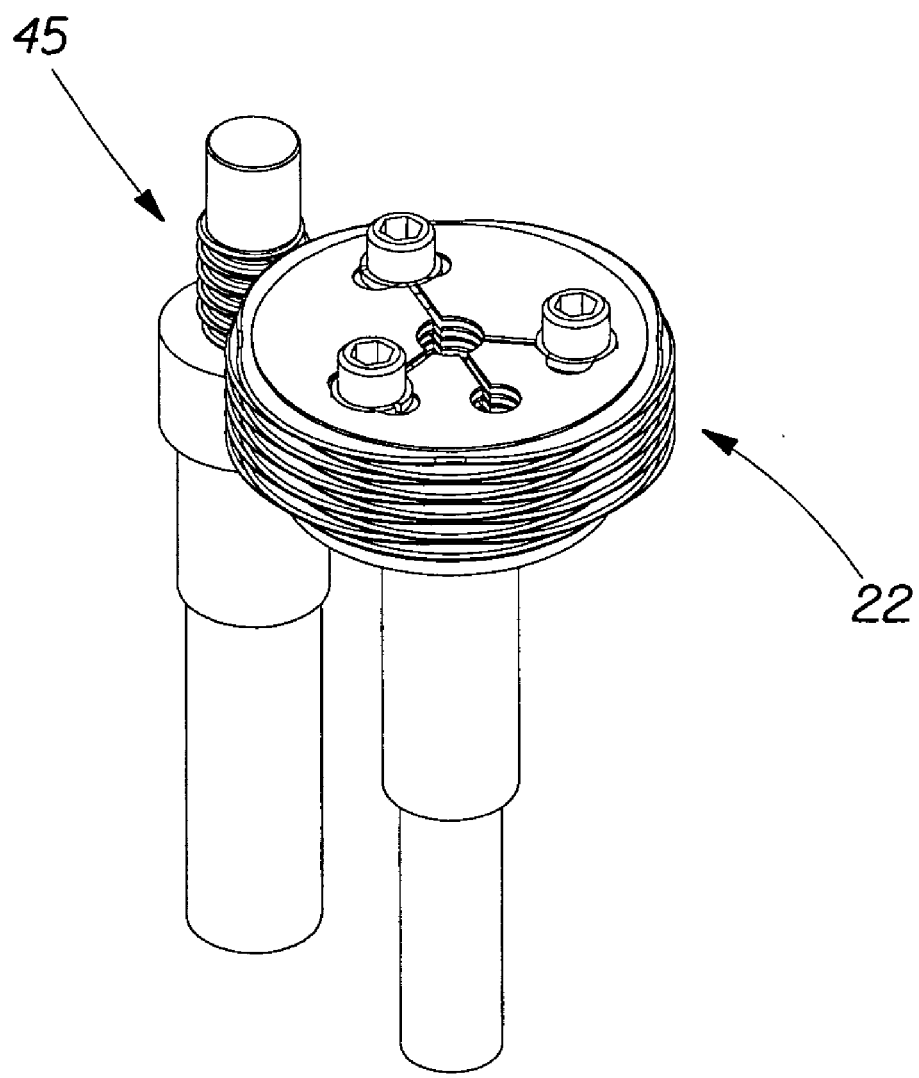
FIG. 12 is a side view of an example of a rotary nip corrugating technique.

Referring to FIG. 5 and FIG. 12, the rotary method forms corrugations 23 about the perimeter or circumference of the tube blank 30 where the corrugating gear and the tube blank 30 are in relative movement to each other about the perimeter. The apparatus in FIG. 5 comprises a guide bushing 21, an outer dye gear 22, and an inner dye gear 45. Further, when using an outer dye gear 22 as a corrugating tool, for example, it may also rotate about its own axis such that it contacts and travels about the perimeter. With the rotary or rotary nip technique, the tube blank 30 being corrugated can be guided between a cantilevered nip consisting of a phased inner dye gear 45 and an outer dye gear 22. Although multiple gears and nips may be used, it is only necessary to provide one nip point in the rotary nip.

The shape, length, texture, and frequency of the mating gears can be modified to impart different corrugation patterns. In the present invention, true involute shape gears are not required to form the pattern because the gears are not used as a power transmission device other than to nip and impart a pattern on the tube (though in some circumstances it could serve a secondary function as power transmission to rotate the tube blank). Since the gear does not necessarily have to transmit power but act as a moving molding or forming service it is broadly defined as "a forming wheel with a shaped or profiled perimeter which is in contact with the tube blank 30 and can form or shape the contacted area of tube blank substrate." The gear can have a regular profile about its perimeter such as being toothed or sinusoidal or it can be irregular in profile. The gear can be located inside or outside the tube blank. It can work in combination with an anvil (e.g. anvil wheel or mandrel) or in combination with another forming gear. The gear, if driven, can be driven by a turning shaft attached to its center axis or driven tangentially by a drive gear. It is preferred that the tip of the gear teeth have some radius such that the nip area is not cut.

Referring to FIG. 5 and FIG. 12, in the rotary process, undersized (to the tube internal diameter) phased gear shapes are used to create alternating peaks and valleys of a corrugate. By adjusting the gap between the gears for tube diameter and caliper one machine can be adjusted to corrugate multiple sizes of tubes. To prevent axial thrust and provide location and alignment, a guide bushing 21 is used to maintain parallelism of the tube axis and the internal mandrel gear axis. The guide bushing 21 can be either located internally at the open end of the tube or externally to the outside of the tube. The guide bushing 21 can either spin with the product or have a small clearance (nominal about 0.127 millimeters or about 0.005 inches) such that the tube is allowed to spin in the bushing. The size of the guide bushing 21 can be from about 8 millimeters to about 25 millimeters. While the guide busing 21 is shown in FIG. 5 to have a circular cross-section, other configurations may be used.

The degrees of rotation of the tube need only be enough to impart the corrugation 23 on the sidewall of the tube. This angle could be as little as 180 degrees (two corrugations) through multiple revolutions of the product. Multiple revolutions may be required to progressively move the material inward thus reducing the circumscribed diameter of the tube.

Referring to FIG. 5 and FIG. 23, the forming gears 22, 45 as described need only be multiples of each other such that they maintain a ridge and valley in phase relationship to each other. In a non-pitch specific gear design the tube will ratchet or oscillate on the internal gear in a plane perpendicular to the axis of the tube. This arrangement allows adjustment for multiple pass corrugation operations to maintain peak and valley phase.

b. Axial Swaging Technique

The axial swaging technique primarily involves a relative motion between the corrugating tool and the tube blank 30 that is different than the rotary technique. With the axial swaging technique, the tool and the tube blank 30 have a relative motion to each other where the tool moves along the length of the tube blank or the tube axis. This motion described is considered axial since its motion is parallel to the tube axis. Using this motion, the corrugation would normally be located at the end of the tube. Alternatively, using this method the entire length of the tube can be creased, creating the predisposition to fold inward when actuated by another process step. This process could be considered as a post forming technique to an existing tube blank in a multitude of materials such as paper, plastic or a combination of materials.

An example of an axial swaging starts by installing the tube blank on either a plane mandrel 26 or one with relief lines axially aligned on the surface much like a gear or the previously mentioned profiled surface. Referring to FIG. 2, a mandrel 26 is shown having a tubular region perimeter 32 which is sized and configured to receive the tube blank 30. In other words, the tube blank 30 must be able to slide onto the tubular region perimeter 32 with only a small amount of clearance therebetween. The purpose of the mandrel is to allow the corrugations 23 on the tube blank 30 to stand on edge like a series of "V's" the relief allows for the legs of the "V" to stand vertically. Too much pressure must not be applied between the forming cup 29 and the mandrel 26. If too much pressure is applied, the corrugations 23 which are formed will collapse forming pleats. The pleats which are the doubling of the material are not desirable because they are more resistant to opening the forward end of the elongate insertion member 17.

Figure 2A:
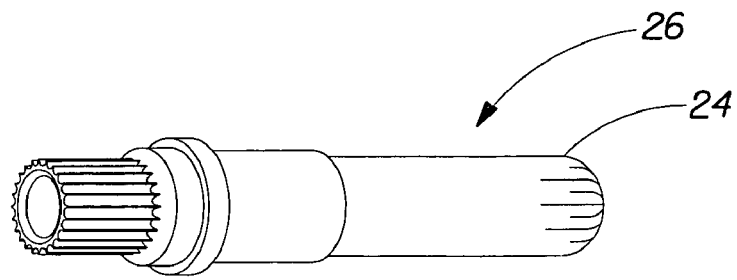
FIG. 2A is an alternative embodiment of the mandrel.

The mandrel 26 has a tip region 27. The mandrel 26 which helps to form the corrugated tip region 27 can be smooth or void of any grooves as shown in FIG. 2. Alternatively, the mandrel 26 can have a configured tip with a plurality of elongated grooves 24 formed therein, as is depicted in FIG. 2A. When the grooves 24 are present, there should be at least two grooves 24, with four grooves most preferred.

The tip region 27 of the mandrel 26 can be formed into a tapered region. Other shapes can also be utilized if desired. It should be noted that the length of the mandrel tubular region 28 is sized to conform closely to the length of the tube blank 30. A typical tube blank 30 will have a length of between about 55 millimeters to about 90 millimeters.

Figure 9:
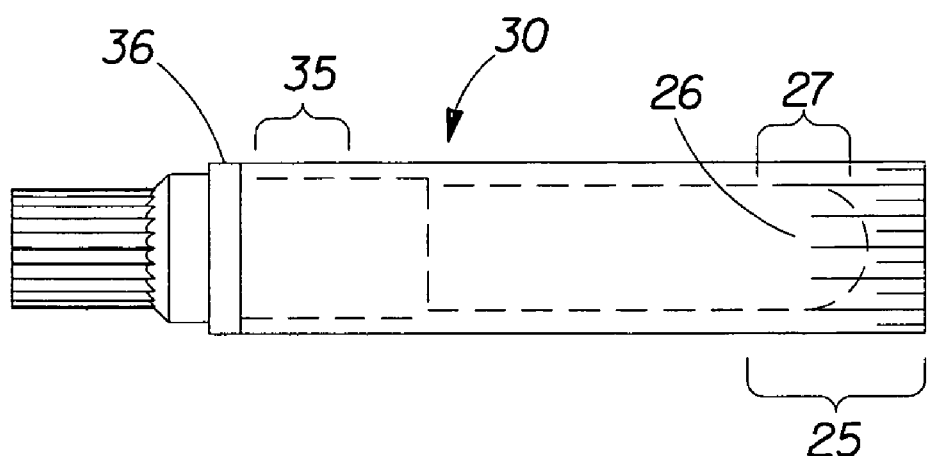
FIG. 9 is a side view of the tube blank placed on the mandrel.
Figure 10:
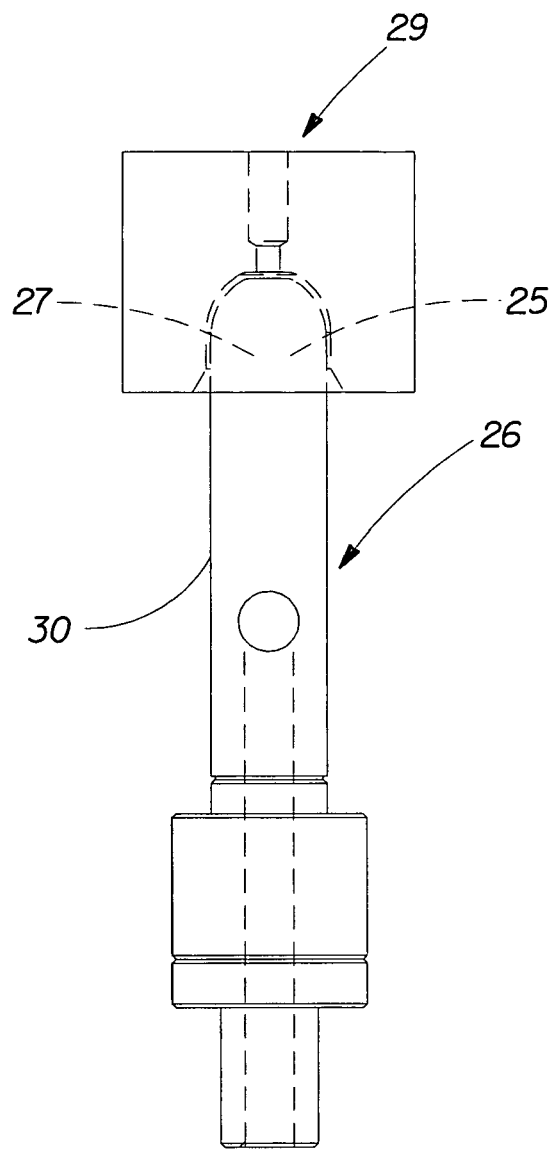
FIG. 10 is a side view of the mandrel in axial engagement with the forming cup.

Referring to FIG. 9, the tubular region 28 should have a length which is equal to, slightly greater, or slightly less than the initial length of the tube blank 30. The first end 25 of the tube blank 30 can be aligned approximately flush with the tip region 27 of the mandrel 26 when the tube blank 30 is positioned on the tubular region 27. However, an extra length of between 65 mm and 80 mm on the tubular region 28 of the mandrel 26 is advantageous for permitting the mandrel 26 to mate with the forming cup 29. When a forming mandrel is used to assist in the formation of the corrugated tip, the mandrel 26 must be relieved to allow for the corrugation 23 depth such that the corrugations are not crushed.

Figure 14:
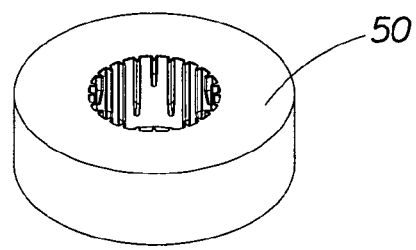
FIG. 14 is a perspective view of the swaging die.

A swaging die 50 is engaged into the product. Referring to FIG. 14, a swaging die is an outer die with protrusions that extend radially inward with a circumscribed diameter across the tip of these protrusions being smaller than the outer diameter of the tube. In the case of a mandrel with no reliefs, the material is compressed between the swaging die 50 protrusions and the mandrel 26, creating fold lines without the normal regions of alternating ridges and troughs. When this tube blank 30 is removed from this mandrel 26 and pressed into a spherically or tapered shaped cup these fold lines will buckle inward creating the troughs of our corrugated tube.

Alternatively, if the aforementioned process uses reliefs in the forming mandrel, phased or in alignment with the protrusions on the swaging die 50, the forming cup 29 will form the alternating ridges and troughs generally called corrugated.

c. Radial Compression Technique

Figure 13:
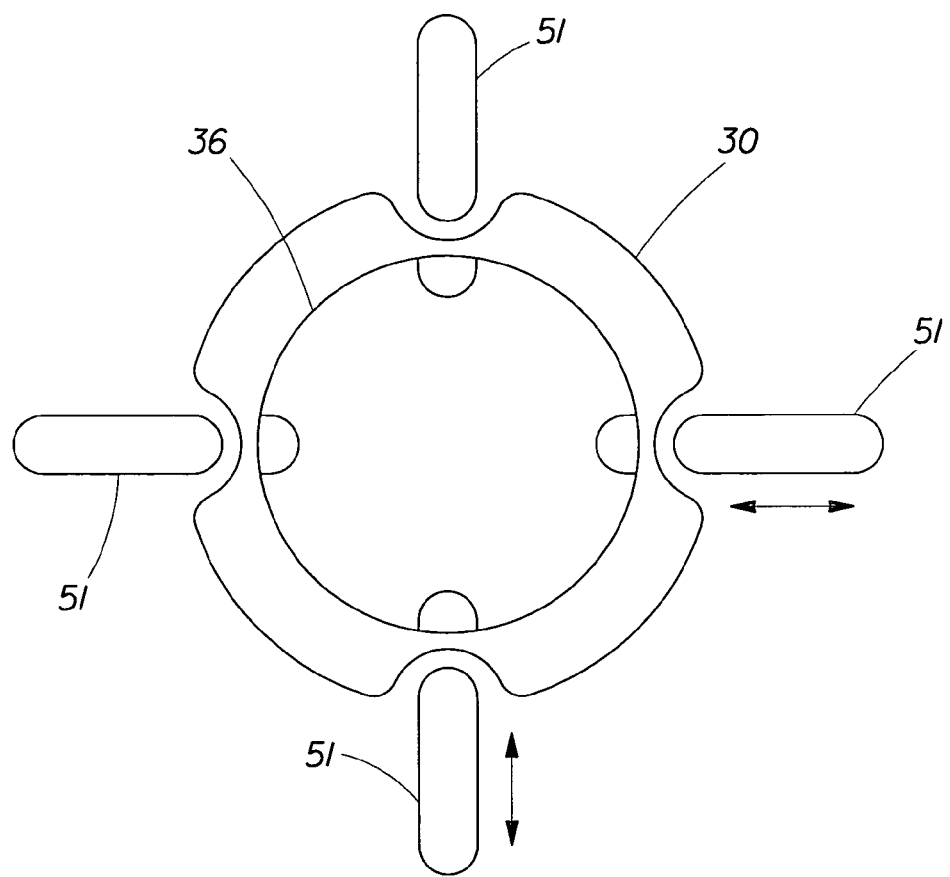
FIG. 13 is a top view of the radial compression technique.

Referring to FIG. 13, the radial compression technique primarily involves a relative motion between the corrugating tool 51 and the tube blank 30 in a radial direction generally perpendicular to length dimension of the tube blank 30. There is at least some inward radial motion whereas the tool or a tool element or elements contact the surface of the tube blank 30 in the region of interest then proceeds further inward thereby penetrating the original perimeter and often drawing some of the tube blank 30 material inward to at least a partial degree. The material can be drawn inward to compress that material and thereby decrease the caliper at that point versus the original caliper, and/or the material caliper can also be displaced inward such that the material is displaced inward beyond the original perimeter of the inside of the tube blank.

Depending on the geometry of the mandrel 36 used for the radial compression, corrugations 23 may be either formed directly in this phase of processing or a predisposition to corrugate along the creases. This method can be performed anywhere along the tube body. When the tube blank is corrugated, the tool 51 may be actuated axially to provide elongated creases or corrugations.

d. Circumscribed Perimeter Reduction Technique

The circumscribed perimeter reduction technique is a technique where one sub-step of the corrugation technique prepares the tube blank for a later sub-step which applies inward directed force in one manner or another to reduce the circumscribed perimeter by the creation of corrugations at the region of interest. As a compressive force is applied, the tube blank begins to collapse in a manner that creates corrugations 23. The first sub-step(s) can comprise the scoring, cutting, perforating, or folding of the substrate in the region of interest such that some form of paper or fiber modification takes place leaving lines of bending where the paper or fiber structure will bend or fold to form corrugations when the later compressive force is applied. Any known means can be utilized to create the lines of bending including some of the approaches described more fully in the softening step section. The compressive force sub-step can be accomplished by any known means whereas the compressive force is applied from the outside via rotary, axial or radially directing tooling and can optionally employ an anvil or mandrel 26 inside the tube blank 30 with the outside tooling can nip or pinch the paper or fiber structure.

While the all the sub-steps of the corrugation step may be performed on the tube blank when the blank is in a non-planar and/or closed form, some of the sub-steps (or even all except for one sub-step) can be executed on the tube blank or its components prior to the tube blank being fully made or shaped into either a closed or non-planar form. For example with the circumscribed perimeter reduction technique the first sub-step can be performed on the paper webs used in a composite tube blank where the tube is formed into a spirally wound, convolutedly wound or longitudinally seamed hollow tube. Then after forming the tube blank and any other intermediate operations, the compressive force sub-step can be executed to complete the formation of the corrugation step. The compressive force sub-step can result in a generally constant circumscribed perimeter of the tube in the area of interest or a changing circumscribed perimeter. Examples of tools for applying a compressive force is a small volume cup mold, a rotary driven wheel, inward radially-directed jaw(s), etc.

3. Final Closure Step

The optional final closure step is most frequently suited to form a tampon tube, which is often meant to be re-opened by the user as she expels the tampon from the tube into the body. Often, the closure can be closed into a variety of geometries as appropriate with examples including spherical, semi-spherical, ellipsoidal and conical configurations.

A closure cup can be used to close a pre-corrugated applicator tube. A tube which has creases in the tube wall, (i.e. no alternating ridges and troughs) will also corrugate with or with out an internal shaped mandrel. The creases will create weakened locations in the circumference of the tube which when axially pressed into the forming cup 29 will complete the corrugation formation process.

Figure 6:
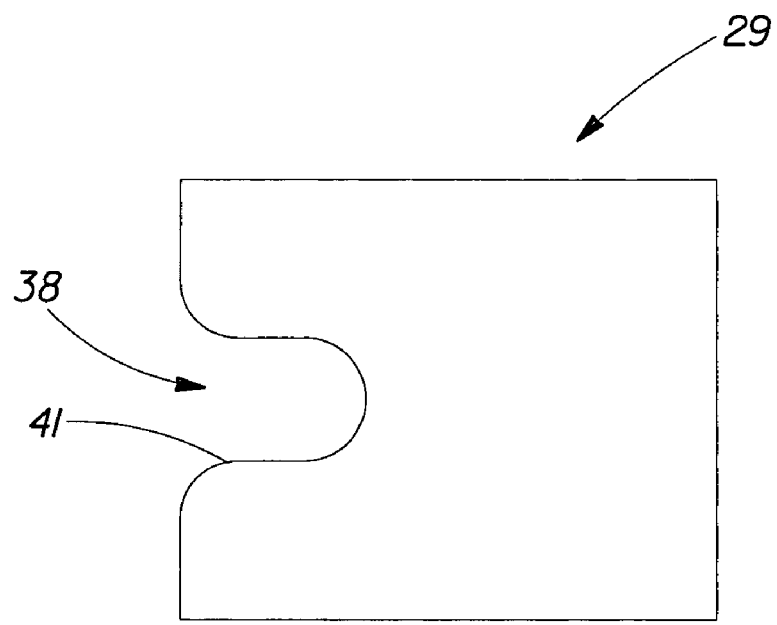
FIG. 6 is a cross-sectional side view of the forming cup.

Referring to FIG. 6, the forming cup 29 is designed to be about 0.127 millimeters to about 0.508 millimeters (about 0.005 inches to about 0.020 inches) larger in diameter than the outside diameter of the product tube to allow the clearances for the formation of the corrugations. The forming cup 29 includes a region which is either conically, spherically, ellipisoidally shaped or some combination of these shapes to complete the corrugation process. In addition to shaping the end of the product, the cup will cause the bend angle between the legs of the corrugations to approach an angle of 180 degrees. When this happens, there may be an opening left in the tip of the closed tube which can be pre-determined algebraically by the number of corrugations times 2 times the wall thickness of the material divided by π (3.14). The forming cup 29 has an inner surface 41 which contacts the first end of the tube blank 30. The inner surface is shaped or profiled to achieve the desired shape of the corrugated tube blank 30. An example of an inner surface 41 of the forming cup 29 with a concave portion is shown in FIG. 6.

Both the forming cup and the mandrel may be heated to further maintain the formed geometry. In addition the cup may be designed such that only certain specific areas are heated such as the tip of the product.

The softening process steps may be combined in this closure stage by the addition of a central pin located in the bottom of the closure cup. This pin could be moved axially into the product tip further flexing the tube materials. This movement would invert the tip of the product further flexing and weakening the tube material. The re-opening the product using a mandrel followed by another formed closure cup. This process would produce a tip with a weaker resistance to opening than one that was only closed once.

While particular embodiments of the present invention have been illustrated and described, it would be obvious to those skilled in the art that various other changes and modifications can be made without departing from the spirit and scope of the invention.

What is claimed is:

1. A method of manufacturing a tampon applicator having a corrugated region, said method comprising the steps of:
 a. providing a guide bushing;
 b. providing a tampon applicator having a first end, a second end, a length and a diameter;
 c. providing an inner dye gear;
 d. providing an outer dye gear;
 e. placing said tampon applicator over said inner dye gear; and
 f. rotating said inner dye gear and said outer dye gear to form a plurality of corrugations in said tampon applicator, said corrugations defining said corrugated region, each of said corrugations having a ridge and a trough.

2. The method of claim 1 wherein said corrugated region forms a grip on said tampon applicator.

3. The method of claim 1 wherein said corrugated region forms a tip on said tampon applicator.

4. The method of claim 1 wherein said corrugated region extends from said first end to said second end of said tampon applicator.

* * * * *

UNITED STATES PATENT AND TRADEMARK OFFICE
CERTIFICATE OF CORRECTION

| | |
|---|---|
| PATENT NO. | : 7,066,870 B2 |
| APPLICATION NO. | : 10/179087 |
| DATED | : June 27, 2006 |
| INVENTOR(S) | : Fedyk et al. |

It is certified that error appears in the above-identified patent and that said Letters Patent is hereby corrected as shown below:

Column 9, line 28, "Fig. 23" should read -- Fig. 12--.

Column 11, line 25, "While the all the sub-steps" should read --While all the sub-steps--.

Signed and Sealed this

Twenty-sixth Day of August, 2008

JON W. DUDAS
*Director of the United States Patent and Trademark Office*